United States Patent [19]

Iwasa

[11] 4,140,754
[45] Feb. 20, 1979

[54] HEMAGGLUTINATION-INHIBITION TEST FOR TOGAVIRUSES

[75] Inventor: Susumu Iwasa, Kyoto, Japan

[73] Assignee: Takeda Chemical Industries, Ltd., Osaka, Japan

[21] Appl. No.: 739,514

[22] Filed: Nov. 8, 1976

[30] Foreign Application Priority Data

Nov. 17, 1975 [JP] Japan .................................. 50-138417

[51] Int. Cl.² ....................... G01N 31/00; G01N 33/16
[52] U.S. Cl. .................................... 424/12; 23/230 B; 195/1.4; 195/63; 195/69; 195/103.5 V; 424/8; 424/86; 424/89
[58] Field of Search ...................... 424/3, 8, 12, 86, 89, 424/93; 23/230 B; 195/63, 69, 103.5, 1.4

[56] References Cited

FOREIGN PATENT DOCUMENTS 48-26913  4/1973  Japan ........................................... 424/12

OTHER PUBLICATIONS

Nakagawa, Chem. Abs., vol. 52, 1958, p. 20389ghi.
Schmidt, Chem. Abs., vol. 75, 1971, Ab. No. 33041r.
Plotkin, Amer. J. of Epidemiology, vol. 88, Nov. 1968, pp. 301–304.
Gupta, Applied Microbiol., vol. 22, 1971, pp. 921–922.
Haukenes, Med. Microbiol. Immunol., vol. 161, No. 2, 1975, pp. 99–106.

Primary Examiner—Anna P. Fagelson
Attorney, Agent, or Firm—Burgess, Ryan and Wayne

[57] ABSTRACT

The non-specific inhibitors of hemagglutination in a subject serum for hemagglutination-inhibition test for a togavirus such as rubella virus can be inactivated by subjecting the subject serum to the action of phospholipase C. By subjecting thus-treated serum to the hemagglutination-inhibition test employing fixed erythrocytes the togavirus hemagglutination-inhibition antibody titer of the serum can be determined accurately and with high sensitivity.

15 Claims, No Drawings

HEMAGGLUTINATION-INHIBITION TEST FOR TOGAVIRUSES

The present invention relates to an improvement in hemagglutination inhibition tests for togaviruses.

The hemagglutination-inhibition test (hereinafter briefly referred to as HI test) of a torgavirus such as rubella virus is more sensitive and more expedient to perform than neutralization and complement-fixation tests, and has been a useful means of serological diagnosis. However, strongly false-positive reactions are encountered with the sera of human and other animals which are normally subjected to such HI tests because these subject sera contain hemagglutination inhibitors nonspecific to the togavirus-specific hemagglutinating antigens. For the purpose of removing those hemagglutination inhibitors, such techniques as kaolin, adsorption and acetone-extraction are commonly employed. In the case of HI tests for rubella virus, precipitation with heparin-$MnCl_2$ or dextran sulfate-$CaCl_2$ has been employed with advantage because of its high reproducibity. However, kaolin is a non-specific adsorbent which adsorbs not only the non-specific inhibitors of hemagglutination but also the hemagglutination-inhibition antibody (hereinafter briefly referred to as HI antibody) itself, thus giving rise to false-negative reactions. Acetone, on the other hand, denatures and inactivates the antibody molecules, thus similarly causing false-negative reactions. In the case of the heparin-$MnCl_2$ or dextran sulfate-$CaCl_2$ method, the reagents must be used in high concentrations to completely remove the non-specific inhibitors of hemagglutination but the practice leads to a poor pattern of hemagglutination and, therefore, to a frequent failure to obtain an accurate readout of the test result. Furthermore, because these techniques invariably require a centrifugation procedure for separating the non-specific inhibitors of hemagglutination from the HI antibody, HI tests on a large scale had to be time-consuming and cumbersome to perform.

With the foregoing as a technical background, the present inventor has unexpectedly found that the non-specific inhibitors of hemagglutination occurring in a subject serum for the HI test for a togavirus can be substantially completely inactivated by allowing phospholipase C to act upon the subject serum without affecting the activity of the togavirus-specfic HI antibody in the serum, and that by subjecting the thus-treated subject serum to the HI test employing fixed erythrocytes the togavirus-specific antibody titer of the subject serum can be determined accurately and with high sensitivity.

Thus, the principal object of the present invention is to provide a novel and advantageous method for inactivating the non-specific inhibitors of hemagglutination in a subject serum for the HI test for a togavirus. Another object is to provide an improved method in the HI test. Other objects will be made clear from the description and claims hereinafter.

Said objects are realized by subjecting the subject serum for the HI test for a togavirus to the action of phospholipase C.

The present invention is applicable to any of togaviruses which are susceptible to HI tests, such as rubella virus, arboviruses (e.g. Japanese encephalitis virus, yellow fever virus, dengue virus, West Nile virus, etc.) and the like. The subject sera may be of any origin that can be subjected to the HI tests for the above-mentioned togaviruses, and are exemplified by the sera of warm-blooded animals such as mammals, e.g. human, cattle, rats, mice, guinea-pigs, and the like. Commonly, human sera are most suitable for the subject sera in the present invention.

According to the present invention, the reaction of phospholipase C upon the subject serum can be smoothly conducted by contacting the former with the latter at a temperature between about 10° C. and about 50° C. The phospholipase C to be employed may be of any origin. Advantageously, phospholipase C is employed in a form of a solution containing about 0.04 to 0.12 unit/ml., especially about 0.06 unit/ml., of phospholipase C in an aqueous solvent (e.g. water, physiological saline, conventional buffers, etc.). This enzymatic treatment may be generally carried out by adding said aqueous solvent solution of phospholipase C to a subject serum or a serum dilution, which is obtained by diluting a subject serum with a conventional diluent, and allowing the mixture to stand at temperatures between about 10° C. and about 50° C., preferably at about 37° C. for about 3 to 20 hours.

By this treatment with phospholipase C, the nonspecific inhibitors of hemagglutination in the subject serum are hydrolyzed and inactivated but the activity of the togavirus-specific HI anitbody occurring in the same serum is not adversely affected in any manner. Unlike the subject sera treated by the known methods employing kaoline, acetone, heparin-$MnCl_2$ or dextran sulfate-$CaCl_2$, the subject serum treated according to this invention does not require a centrifugation step which is usually required for separating the non-specific inhibitors of hemagglutination from the togavirus-specific HI anitbody. Thus, merely after it has been inactivated in the conventional manner (for example by incubation at 56° C. for 30 minutes) and, if desired, diluted, the serum can be subjected to togavirus HI tests. It should be understood that the object of the present invention, i.e. inactivating the hemagglutination inhibitors non-specific to togavirus-specific hemagglutinating antigens, can not be accomplished by allowing any of phospholipase A, B and D to act upon the subject sera.

In accordance with the present invention, the togavirus HI antibody titer can be determined accurately and with high sensitivity by carrying out a toavirus HI test using a subject serum in which any non-specific hemagglutination inhibitor has been inactivated in the above-described manner. In this connection, although fresh erythrocytes are hemolyzed by the phospholipase C remaining in the serum, the fixed erythrocytes were found, surprisingly, to be not hemolyzed at all by phospholipase C, thus giving a well-defined pattern of hemagglutination.

The erythrocytes may be any erythrocytes that can be agglutinated by togavirus-specific hemagglutinating antigens. Thus, for example, the erythrocytes of mammals (sheep, monkeys and human "O" group) and fowl [chicken (chicks and adults), geese, pigeons, quails, etc.] can be used with advantage. The fixation of such erythrocytes may be carried out in any manner known per se. Thus, formalinized erythrocytes are particularly advantageous. For example, the formalinized erythrocytes of one-day-old chicks described in e.g. Japanese Patent Application Laid-Open No. 26913/1973 may be put to use with advantage.

The HI tests may be conducted in the manner known per se. Thus, the subject serum in which any non-specific inhibitors of hemagglutination have been inactivated with phospholipase C is mixed with a togavirus-specific hemagglutinating antigen and further with the fixed erythrocytes to assess the occurrence or non-occurrence of hemagglutination. In performing this HI test, use may be made of any technique applicable for togavirus HI tests, such as the microtiter method. For example, such a togavirus HI test may be performed as follows. Thus, 0.025 ml. of a subject serum with inactivated non-specific hemagglutination inhibitors is serially diluted in two-fold steps on a microplate and 0.025 ml. of a togavirus-specific hemagglutinating antigen with 4 hemagglutination untis is added. The system is allowed to stand at room termperature for 30 minutes, after which time 0.050 ml. of a 0.25% suspension of fixed erythrocytes is mixed with the above preparation. The system is allowed to stand at room temperature for 60 minutes and the occurrence or non-occurrence of hemagglutination is investigated. The togavirus HI antibody titer is the reciprocal of the highest dilution factor of the subject serum with completely inhibited hemagglutination. By this procedure, the togavirus HI antibody titer of the subject serum can be determined with accuracy and high sensitivity.

The following Examples and Experimentals are merely intended to illustrate presently preferred embodiment of this invention and not to restrict the scope of this invention.

Throughout the present specification as well as in claims, the "mg.", "g.", "ml.", "° C.", "M" and "N" respectively refer to "milligram(s)", "gram(s)", "milliliter(s)", "degrees centigrade", "molar concentration" and "normality", and percentages are weight/volume unless otherwise specified.

EXAMPLE 1

To 0.1 ml. of a subject human serum for togavirus HI test was added 0.2 ml. of HSAG*[1)], and 0.1 ml. of a 0.6 unit/ml. aqueous solution of phospholipase C*[2)] was added. The mixture was incubated at 37° C. overnight. Then, it was incubated at 56° C. for 30 minutes. By this procedure the non-specific inhibitors of hemagglutination in the subject serum were inactivated.

*[1)] HSAG, for HEPES-Saline-Albumin-Gelatin, has the following composition.

| | |
|---|---|
| HEPES (N-2-hydroxyethylpiperazine-N'-2'-ethanesulfonic acid) | 2.97 g. |
| NaCl | 4.09 g. |
| CaCl$_2$(anhydrous) | 55.5 mg. |
| Bovine serum albumin | 1.0 g. |
| Gelatin | 1.25 mg. |

The above ingredients are dissolved in 400 ml. of distilled water and the solution is adjusted to pH 6.2 with 1N-NaOH and made up with ditilled water to make 500 ml.

*[2)] The phospholipase C used is a commercial product prepared from Clostridium perfringens ("Phospholipase C" prepared and sold by P-L Biochemicals, Inc., Milwaukee, U.S.A.), one unit of this enzyme being capable of liberating 1 micromole of the acid-soluble phosphorus (phosphorus of phosphorylcholine) per minute when allowed to act upon lecithin at pH 7.3 and 37° C.

EXAMPLE 2

The procedure of Example 1 was repeated except that VBS*[3)] or PBS*[4)] was used in place of HSAG to inactivate the non-specific inhibitors of hemagglutination in subject human sera.

*[3)] VBS, for Veronal-Buffered Saline, has the following composition.

| | |
|---|---|
| 5 × Veronal buffer | 200 ml. |
| CaCl$_2$ (anhydrous) | 0.2 g. |
| MgCl$_2$ . 6H$_2$O | 0.2 g. |
| Bovine serum albumin | 1.0 g. |
| Gelatin | 10 mg. |

The above ingredients are diluted with distilled water to make 1000 ml.

*[4)] PBS, for Phosphate-Buffered Saline, has the following composition.

| | |
|---|---|
| NaCl | 8.0 g. |
| KCl | 0.2 g. |
| KH$_2$PO$_4$ | 0.2 g. |
| Na$_2$HPO$_4$ . 2H$_2$O | 1.44 g. |
| CaCl$_2$ (anhydrous) | 0.1 g. |
| MgCl$_2$ . 6H$_2$O | 0.1 g. |
| Bovine serum albumin | 2.0 g. |
| Gelatin | 10 mg. |

The above ingredients are dissolved in distilled water to make 1000 ml.

EXAMPLE 3

Bovine, rat, mouse and guinea-pig sera were treated in the same manner as Example 1, whereby the non-specific inhibitors of hemagglutination therein were inactivated.

EXPERIMENTAL 1

Comparison of untreated serum, phospholipase C-treated serum, kaolin-treated serum and dextran sulfate-CaCl$_2$-treated serum in rubella virus HI test From each of subject human sera, the following untreated and pretreated sera, (a) to (d), were prepared.

(a) Untreated serum 0.1 ml. of the subject serum was diluted with 0.6 ml. of HSAG.

(b) Phospholipase C-treated serum 0.4 ml. of the phospholipase C-treated serum according to Example 1 was diluted with 0.3 ml. of HSAG.

(c) Kaolin-treated serum

To 0.1 ml. of the subject serum was added 0.3 ml. of HSAG. To this diluted serum was added 0.4 ml. of a 25% suspension of kaolin. The mixture was incubated at 30° C. for 30 minutes, after which time it was centrifuged. The supernatant was separated and incubated at 56° C. for 30 minutes to inactivate the serum.

(d) Dextran sulfate-CaCl$_2$-treated serum

To 0.1 ml. of the subject serum was added 0.4 ml. of HSAG. Then, 0.1 ml. each of 1% dextran sulfate and 0.5MCaCl$_2$ were added to the diluted serum. The mixture was allowed to stand at 4° C. for 60 minutes and, then, centrifuged. The supernatant was taken and incubated at 56° C. for 30 minutes to inactivate the serum.

To each of the above sera, (a) to (d), was added 0.1 ml. of a 10% suspension of the formalinized erythrocytes described hereinafter to absorb the natural agglutinins, before use in the HI test.

For the phospholipase C-treated serum (b), both the formalinized erythrocytes of one-day-old chicks (the lyophilized erythrocytes prepared according to Example 1 of Japanese Patent Application Laid-Open No. 26913/1973 as resuspended in distilled water) and fresh erhthrocytes of one-day-old chicks were employed, while the aforementioned formalinized erythrocytes only were employed for the other pretreated sera. By the microtiter technique of Sever [Journal of Immunology 88 (1962), 320–329], the rubella virus HI antibody titers of the subject sera were determined using permanent V-type plates. The dilution of sera, HA antigen and the erythrocytes was all performed with HSAG.

The results are set forth in Table 1.

Table 1

| Subject serum | Rubella virus HI titer | | | | Fresh erythrocytes (b) Phospholipase C-treated |
|---|---|---|---|---|---|
| | Formalinized erythrocytes | | | | |
| | (a) Untreated | (b) Phospholinipase C-treated | (c) Kaolin-treated | (d) Dextran sulfate-CaCl$_2$-treated | |
| 1 | 512 | 64 | 32 | 64 | * |
| 2 | 1024 | 32 | 16 | 64 | * |
| 3 | 2048 | <8 | <8 | <8 | * |
| 4 | 512 | 64 | 16 | 64 | * |
| 5 | 2048 | 64 | 16 | 32 | * |
| 6 | 1024 | 16 | 8 | 16 | * |
| 7 | 256 | <8 | <8 | <8 | * |
| 8 | 256 | <8 | <8 | <8 | * |
| 9 | 256 | 32 | 32 | 32 | * |
| 10 | 2048 | 32 | 32 | 64 | * |
| 11 | 512 | <8 | <8 | 8 | * |
| 12 | 1024 | 128 | 128 | 128 | * |

*Because of a lysis of erythrocytes that had taken place, the pattern of hemagglutination was not sufficiently well-defined to permit an assessment of the HI titer.

The rubella virus HI tests employing the phospholipase C-treated sera were repeated except that the formalinized erythrocytes of one-day-old chicks were replaced by the formalinized erythrocytes of adult chicken, one-day-old goose or sheep, whereby the results similar to those for "phospholipase C-treated" in Table 1 were obtained.

EXPERIMENTAL 2

Comparison of untreated serum, phospholipase C-treated serum and acetone-treated serum in Japanese encephalitis virus HI test:

For each of the subject human sera, the following untreated and pretreated sera, (e) to (g), were prepared.

(e) Untreated serum 0.1 ml. of the subject serum was diluted with 0.6 ml. of a 0.01M-aqueous solution of sodium borate.

(f) Phospholipase C-treated serum 0.4 ml. of the phospholipase C-treated serum prepared with the employment of PBS according to Example 2 was diluted with 0.3 ml. of a 0.01M-aqueous solution of sodium borate.

(g) Acetone-treated serum

To 0.1 ml. of the subject serum was added 2 ml. of acetone and the mixture was centrifuged at 1500 r.p.m. for 5 minutes. The supernatant was discarded and, following the addition of another 2 ml. of acetone, the serum was cenrifuged again. The supernatant was discarded. The sediment was dried and 0.7 ml. of a 0.01M-aqueous solution of sodium borate was added. The mixture was allowed to stand at 4° C. overnight.

To each of the above sera (e) to (g), 0.1 ml. of a 10% suspension of the formalinized erythrocytes of one-day-old chicks referred to in Experimental 1 was added to absorb the natural agglutinins befoe subjecting it to the HI test.

For each of the sera, the Japanese encephalitis virus HI titer was determined by the microtiter method of Clarke et al [American Journal of Tropical Medicine and Hygiene 7 (1958), 561–573] using permanent V-plates with the employment of the formalinized erythrocytes of one-day-old chicks, The results are given in Table 2.

Table 2

| Subject serum | Japanese encephalitis virus HI titer | | |
|---|---|---|---|
| | (e) Untreated | (f) Phospholipase C-treated | (g) Acetone-treated |
| 1 | 8 | <8 | <8 |
| 2 | 256 | 128 | 128 |
| 3 | 8 | 8 | <8 |
| 4 | 8 | <8 | <8 |
| 5 | 16 | <8 | <8 |
| 6 | 32 | 16 | 8 |
| 7 | 8 | <8 | <8 |
| 8 | 64 | 32 | 16 |
| 9 | 64 | 64 | 64 |
| 10 | 8 | <8 | <8 |
| 11 | 16 | 8 | 8 |
| 12 | 16 | 8 | <8 |

What is claimed is:

1. In a hemagglutination-inhibition test for a togavirus which comprises inactivating the non-specific inhibitors of hemagglutination occurring in a subject serum, mixing the subject serum with a togavirus-specific hemagglutinating antigen and then with erythrocytes to assess occurrence of hemagglutination, the improvement comprising (1) preparing the subject serum for testing by contacting said serum with a solution containing about 0.04 to 0.12 units/ml of phospholipase C in an aqueous solvent for a time sufficient to inactivate the nonspecific inhibitors before the mixing with the antigen, and (2) employing fixed erythrocytes as the erythrocytes.

2. The method according to claim 1, wherein the subject serum is contacted with phospholipase C at about 37° C. for about 3 to 20 hours.

3. The method according to claim 1, wherein the fixed erythrocytes are formalinized erythrocytes.

4. The method according to claim 1, wherein the togavirus is rubella virus.

5. The method according to claim 1, wherein the phospholipase C solution contains about 0.06 unit/ml of phospholipase C.

6. The method according to claim 1, wherein the subject serum is of warm-blooded animal origin.

7. The method according to claim 6, wherein the warm-blooded animal is human.

8. The method according to claim 1, wherein the subject serum is contacted with phospholipase C at a temperature between about 10° C. and about 50° C.

9. The method according to claim 8, further comprising incubating the mixture of serum and phospholipase C at 56° C. for 30 minutes after said contacting at about 10° to about 50° C.

10. The method according to claim 1, wherein the fixed erythrocytes are of warm-blooded animal origin.

11. The method according to claim 10, wherein the warm-blooded animal is fowl.

12. The method according to claim 11, wherein the fowl is chick.

13. The method according to claim 1, wherein said serum is diluted with a diluent selected from the group consisting of HEPES-Saline-Albumin-Gelatin, Veronal-Buffered Saline and Phosphate-Buffered Saline.

14. The method according to claim 13, wherein said diluent is HEPES-Saline-Albumin-Gelatin.

15. The method according to claim 13, further comprising serially diluting the serum in two-fold steps using said diluent.

* * * * *

UNITED STATES PATENT OFFICE
CERTIFICATE OF CORRECTION

Patent No. 4,140,754         Dated    February 20, 1979

Inventor(s)  Susumu Iwasa

It is certified that error appears in the above-identified patent and that said Letters Patent are hereby corrected as shown below:

Column 1, line 22:  "producibity" should be --producibility--.

Columm 2, line 45:  "toavirus" should be --togavirus--.

Column 3, line 52:  "ditilled" should be --distilled--.

Column 4, line 60:  "erhthrocytes" should be --erythrocytes--.

Column 5, Table 1, heading (b):  "Phospholinipase" should be --Phospholipase--.

line 50:  cenrifuged" should be --centrifuged--.

Signed and Sealed this

Twenty-fourth Day of July 1979

[SEAL]

Attest:

LUTRELLE F. PARKER

Attesting Officer    Acting Commissioner of Patents and Trademarks